US009181168B2

United States Patent
Ditzel

(10) Patent No.: US 9,181,168 B2
(45) Date of Patent: Nov. 10, 2015

(54) PROCESS FOR THE PRODUCTION OF METHYL ACETATE/ACETIC ACID

(75) Inventor: Evert Jan Ditzel, Howden (GB)

(73) Assignee: BP CHEMICALS LIMITED, Middlesex (GB)

(*) Notice: Subject to any disclaimer, the term of this patent is extended or adjusted under 35 U.S.C. 154(b) by 5 days.

(21) Appl. No.: 13/981,935

(22) PCT Filed: Jan. 24, 2012

(86) PCT No.: PCT/GB2012/000068
§ 371 (c)(1),
(2), (4) Date: Jul. 26, 2013

(87) PCT Pub. No.: WO2012/101403
PCT Pub. Date: Aug. 2, 2012

(65) Prior Publication Data
US 2013/0310599 A1    Nov. 21, 2013

(30) Foreign Application Priority Data
Jan. 27, 2011 (EP) .................................. 11250091

(51) Int. Cl.
C07C 51/12 (2006.01)
C07C 67/37 (2006.01)
C07C 67/03 (2006.01)
B01J 29/90 (2006.01)
B01J 29/22 (2006.01)
B01J 29/24 (2006.01)

(52) U.S. Cl.
CPC .................. $C07C\ 51/12$ (2013.01); $B01J\ 29/22$ (2013.01); $B01J\ 29/24$ (2013.01); $C07C\ 67/03$ (2013.01); $C07C\ 67/37$ (2013.01); $B01J\ 29/90$ (2013.01)

(58) Field of Classification Search
CPC ............ B01J 29/22; B01J 29/24; B01J 29/90; C07C 51/12; C07C 67/03; C07C 67/37
USPC .......................................... 560/232; 562/519
See application file for complete search history.

(56) References Cited

U.S. PATENT DOCUMENTS 8,158,815 B2* 4/2012 Ditzel et al. ................... 560/232
8,431,732 B2* 4/2013 Armitage et al. ............. 560/232

FOREIGN PATENT DOCUMENTS

| EP | 2 072 124 A1 | 6/2009 | |
| WO | WO 2009/077739 A1 | 6/2009 | |
| WO | WO 2009/077743 A1 | 6/2009 | |
| WO | WO2009/077745 * | 6/2009 | ............... B01J 29/90 |

OTHER PUBLICATIONS

PCT Notification of Transmittal of the International Search Report and the Written Opinion of the International Searching Authority, or the Declaration; mailed Mar. 26, 2012; PCT/GB2012/000068, Intl Filing Date Jan. 24, 2012, 12 pgs.

* cited by examiner

*Primary Examiner* — Paul A Zucker
*Assistant Examiner* — Mark Luderer
(74) *Attorney, Agent, or Firm* — Nixon & Vanderhye P.C.

(57) ABSTRACT

Process for the production of methyl acetate and/or acetic acid by contacting a carbon monoxide-containing gas and methanol and/or reactive derivatives thereof with a mordenite loaded with copper and silver loaded by ion-exchange and subsequently regenerating the catalyst.

23 Claims, 1 Drawing Sheet

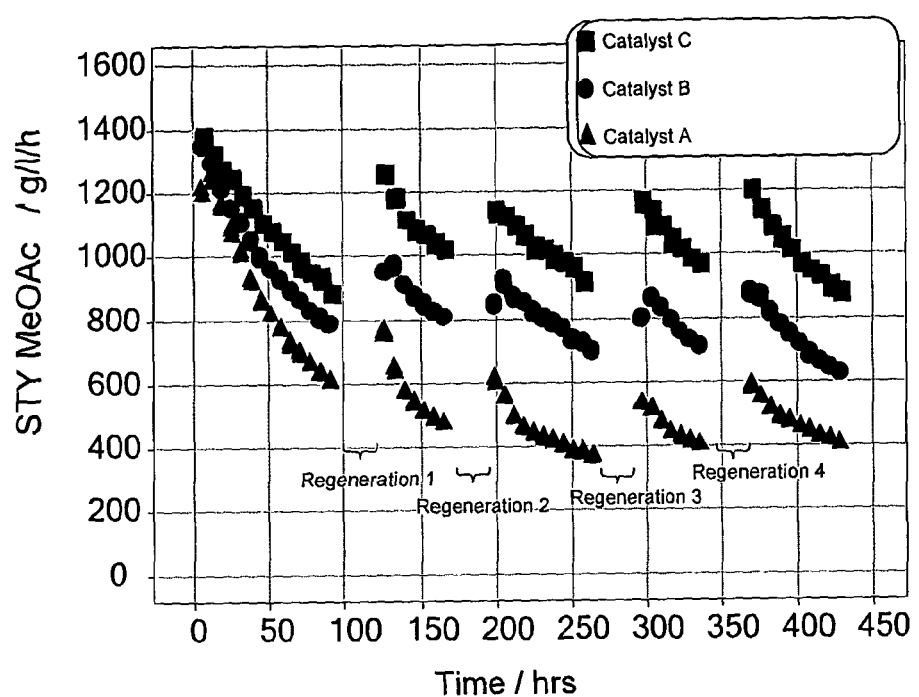

PROCESS FOR THE PRODUCTION OF METHYL ACETATE/ACETIC ACID

This application is the U.S. national phase of International Application No. PCT/GB2012/000068 filed 24 Jan. 2012 which designated the U.S. and claims priority to European Patent Application No. 11250091.3, filed 27 Jan. 2011, the entire contents of each of which are hereby incorporated by reference.

This invention relates to a carbonylation process for the production of methyl acetate and/or acetic acid in the presence of catalyst which is subsequently regenerated, and, in particular to a carbonylation process wherein the catalyst is a mordenite loaded with copper and silver by ion-exchange.

BACKGROUND OF THE INVENTION

Mordenites are known to catalyse the carbonylation of feedstocks such as methanol and dimethyl ether with carbon monoxide to produce methyl acetate and/or acetic acid products. For use as catalysts in carbonylation processes, mordenites can be used in a number of different forms, including the proton form and metal modified forms.

Techniques for the preparation of metal modified forms of mordenite, such as slurry impregnation or ion-exchange are well-known. For example, WO 2009/077743 describes the loading of mordenite with a Group IB metal by the techniques of ion-exchange and slurry impregnation. WO 2010/067043 describes the preparation of mordenite catalysts by compositing a mordenite which has been pre-loaded with at least one of copper and silver, with an inorganic oxide binder.

The activity of mordenite catalysts, for the carbonylation of methanol and/or dimethyl ether to produce acetic acid and/or methyl acetate decreases as the run time increases and the catalysts then have to be regenerated. Regeneration processes are, for example, described in WO 2009/077745 and WO 2009/077739.

WO 2009/077745 describes a regeneration process wherein a mordenite catalyst is regenerated by contacting the catalyst with a molecular-oxygen containing gas and an inert diluent at a pressure of 1 to 100 bar whilst maintaining the catalyst at a temperature of 225 to 325° C.

WO2009/077739 describes a regeneration process wherein a zeolite catalyst is regenerated by contacting the catalyst with hydrogen or a mixture of hydrogen and carbon monoxide at a temperature in the range 250 to 600° C.

However, the regeneration process, and especially when repeated a number of times, can have an adverse effect on space time yield and catalyst lifetime.

SUMMARY OF THE INVENTION

It would therefore be desirable to provide a mordenite catalyst which is more effectively regenerated in a carbonylation process for the production of methyl acetate and/or acetic acid from methanol and/or reactive derivatives thereof, and, in particular, a mordenite catalyst which is more effectively regenerated following multiple regenerations, thereby allowing improved space time yields subsequent to regeneration to be achieved.

It has now been found that mordenites loaded with both copper and silver by the technique of ion-exchange exhibit superior regeneration characteristics than mordenites loaded with either copper or silver alone.

Accordingly, the present invention provides a process for the production of at least one of methyl acetate and acetic acid which process comprises contacting in a reactor a carbon monoxide-containing gas and a carbonylatable reactant selected from at least one of methanol and reactive derivatives thereof with a catalyst which comprises a mordenite loaded with copper and silver, the loading of the copper and silver being carried out by ion-exchange of part or all of the cation-exchangeable sites of the mordenite with copper and silver ions, to produce at least one of methyl acetate and acetic acid and subsequently regenerating the catalyst.

The catalyst for use in the process of the present invention comprises a mordenite which is loaded with copper and silver by the ion-exchange of part or all of the cation-exchangeable sites of the mordenite.

Mordenite is commercially available in a number of cation-exchangeable forms, including the sodium and the ammonium and proton forms. Mordenite in any one of these forms is suitable for ion-exchange with copper and silver, but preferably, the ammonium or proton form of mordenite is used.

Ion-exchange is a well-known technique for exchanging up to 100% of cation-exchangeable sites of a zeolite by metal cations. A suitable ion-exchange method for replacing part or all of the cation-exchangeable sites of mordenite with copper and silver metal cations, is that described, for example, in WO2009/077743.

The loading of copper and silver onto the mordenite may be carried out by simultaneous or sequential ion-exchange, preferably by sequential ion-exchange.

If simultaneous ion-exchange is to be performed, mordenite is contacted with an aqueous solution containing a copper salt and a silver salt.

If sequential ion-exchange is to be carried out, mordenite is contacted with an aqueous solution of a salt of a first metal to produce a metal loaded mordenite followed by contacting the metal loaded mordenite with an aqueous solution of a salt of a second metal. The first metal may be copper or silver and the second metal may be copper or silver. Suitably, the first metal is silver and the second metal is copper.

Copper salts which are suitable for loading onto mordenite by ion-exchange may be copper (I) salts or copper (II) salts or a mixture thereof.

Suitable copper (I) salts include copper halides, such as copper chloride, and copper acetate.

Suitable copper (II) salts include copper nitrate, copper acetate, copper sulphate, copper oxalates, and copper halides such as copper chloride.

Silver salts which are suitable for loading onto mordenite by ion-exchange include silver nitrate, silver acetate and silver triflate.

In the presence of white light silver salts tend to undergo light promoted reduction to silver metal so it is preferred that ion-exchange with silver is carried out in the substantial absence of light.

Aqueous solutions of copper and/or silver salts may be formed by dissolving the metal salts in any suitable solvent. Suitable solvents include deionised water and a solution of ammonium hydroxide in deionised water.

Mordenite may be loaded with copper and/or silver by ion-exchange in accordance with the following steps:

(1) contacting the mordenite with at least one aqueous solution of a metal salt selected from copper and/or silver salts until the mordenite is at or above its level of incipient wetness (2) filtering the contacted mordenite to obtain a solid copper and/or silver loaded mordenite (3) washing the copper and/or silver loaded mordenite with a solvent (4) drying the washed copper and/or silver loaded mordenite (5) where necessary, steps (1) to (5) are repeated so as to obtain a mordenite loaded with both copper and silver.

This procedure may further comprise the additional steps:

(6) prior to filtering the contacted mordenite obtained in step 2, the contacted mordenite is heated (7) optionally compositing the dried mordenite of step 4 or step 5 with a binder material (8) calcining the dried catalyst obtained in step 4 or step 5 or the bound catalyst obtained in step (7)

The processes of these steps will be described in further detail below. The term 'metal salt' means one or more metal salts selected from copper and silver salts.

The contacting of the mordenite with an aqueous solution of metal salt is continued until the mordenite is at or above its level of incipient wetness.

Subsequent to contacting of the mordenite with the aqueous solution of metal salt, the mordenite/metal salt solution may be filtered to remove excess metal salt solution and to recover a solid metal loaded mordenite. Filtration of the mordenite/metal salt solution may be carried out using conventional filtration techniques such as vacuum filtration.

Heating the mordenite/metal salt solution has been found to improve the rate of metal exchange onto the mordenite. Thus, preferably, and, where carried out, prior to filtering of the mordenite/metal salt solution, the mordenite/metal salt solution is heated. Heating may be carried out at any suitable temperature provided that the level of incipient wetness is maintained and any residual metal salt solution remains as a solution. At atmospheric pressure, a suitable temperature may be in the range 60 to 110° C. The mordenite/metal salt solution may be heated until the desired level of metal loading is reached.

After filtering, the solid metal loaded mordenite may be washed to remove residual metal salt solution. Washing may be carried out with a solvent in which the metal salt solution is soluble. Preferably, the solvent employed does not remove copper and silver which has been loaded onto the mordenite. Suitable solvents include deionised water.

The washed metal loaded mordenite may be dried to remove residual water to obtain a free-flowing powder. Suitably, drying is carried out by heating the metal loaded mordenite to a temperature of at least 90° C., for example 90 to 120° C. Heating may be conducted in static or free-flowing air or in an inert gas such as nitrogen.

If sequential loading of a mordenite is carried out, the dried mordenite loaded with a first metal is then contacted with an aqueous solution of the second metal and the process of optional heating, filtering, washing and drying is repeated.

Suitably, mordenite is loaded with copper and silver by ion-exchange in a combined amount in the range 5 to 200 mol % relative to the total aluminium content of the mordenite. By total aluminium content is meant the combined amount of framework aluminium and, if present, extra-framework aluminium.

The mol % metal loading relative to aluminium can be calculated through the relationship:

mol % metal=(gram atoms of metal/gram atoms of aluminium)×100

Preferably, the combined copper and silver loading relative to aluminium is in the range 10 to 100 mol %, such as 10 to 60 mol %.

Suitably, the copper loading relative to aluminium is in the range 5 to 30 mol %

Suitably, the silver loading relative to aluminium is in the range 5 to 50 mol %.

Preferably, the copper and silver loaded mordenites for use in the process of the present invention are prepared from mordenites having a silica:alumina ratio in the range 15:1 to 90:1.

A prepared copper and silver loaded mordenite may be extruded or pelleted according to procedures known in the art.

Alternatively, a copper and silver loaded mordenite may be combined with an inorganic oxide that serves as a binder material. Preferred inorganic oxide binder materials include silicas, aluminas, silica-aluminas, magnesium silicates, magnesium aluminium silicates, titanias, zirconias and clays, and, in particular, aluminas and silica-aluminas.

The copper and silver loaded mordenite may be combined with a binder material by any method known in the art. Suitable methods include those described in WO 2010/067043.

Preferably, prior to use as a catalyst in the process of the present invention, the copper and silver loaded mordenite is calcined. Suitably, calcination is carried out by heating the mordenite at a temperature in the range 400 to 600° C. and may be carried out in static or free-flowing air or in an inert gas such as nitrogen.

The mordenites loaded with copper and silver by ion-exchange are used as catalysts in the process of the present invention to catalyse the carbonylation of methanol and/or a reactive derivative thereof with a carbon monoxide-containing gas to produce at least one of methyl acetate and acetic acid.

Reactive derivatives of methanol which may be used as an alternative to, or in addition to methanol, include methyl acetate and dimethyl ether. A mixture of methanol and a reactive derivative thereof, for example a mixture of methanol and methyl acetate, also may be employed. If dimethyl ether is used as the carbonylatable reactant, it may be generated in-situ from any suitable source, such as dimethyl carbonate. For example, liquid dimethyl carbonate may be contacted with gamma-alumina to decompose the dimethyl carbonate to dimethyl ether and carbon dioxide.

Depending on the nature of the carbonylatable reactant used, the carbonylation process may be carried out under hydrous or substantially anhydrous conditions.

Preferably, where methyl acetate is used as the carbonylatable reactant, the process is carried out under hydrous conditions. Suitably, water may be present in the feed at a molar ratio of methyl acetate:water in the range 50:1 to 2:1.

Where the carbonylatable reactant is dimethyl ether, water has been found to inhibit the carbonylation process, thus it is preferred that when using dimethyl ether as a reactant, the process is carried out under anhydrous conditions. By 'anhydrous' is meant that, in the process, water is kept as low as is feasible. Suitably, water may be present in the gaseous carbonylatable reactant feed(s) in a total combined amount of less than 2.5 wt %, for example, less than 0.5 wt % relative to the amount of dimethyl ether introduced into the process. To accomplish this, the dimethyl ether, the carbon monoxide-containing gas and catalyst are preferably dried prior to introduction into the process.

The carbonylation process employs a carbon monoxide-containing gas. Suitably, the carbon monoxide-containing gas is carbon monoxide or a mixture of carbon monoxide and hydrogen.

The carbon monoxide may comprise small amounts of inert impurities such as nitrogen and the noble gases.

Suitably, the carbon monoxide-containing gas may comprise a molar ratio of carbon monoxide to hydrogen in the range 1:3 to 15:1, such as 1:1 to 10:1.

Mixtures of carbon monoxide and hydrogen for use as the carbon monoxide-containing gas may be those produced by the steam reforming, autothermal reforming or partial oxidation of hydrocarbons, such as methane. These carbon monoxide and hydrogen containing mixtures are conventionally referred to as synthesis gas. Synthesis gas may comprise carbon monoxide to hydrogen at a molar ratio in the range 1:3 to 15:1, such as 1:1 to 10:1.

The carbonylation process may suitably be carried out at a temperature in the range of 100° C. to 400° C., such as 150 to 350° C.

The carbonylation process may be carried out at a total pressure in the range 1 to 100 barg, such as 10 to 100 barg.

The molar ratio of carbon monoxide to carbonylatable reactant is suitably in the range 1:1 to 99:1, such as 1:1 to 60:1.

Where hydrogen is present in the carbonylation process, hydrogen may be present at a partial pressure of at least 0.1 barg, such as 1 to 30 barg.

The gas hourly space velocity (GHSV) is suitably in the range 500 to 40,000 $h^{-1}$, such as 2000 to 10,000 $h^{-1}$.

Prior to use in the carbonylation process, the catalyst may be activated by, for example, by subjecting it to elevated temperature for at least one hour under flowing nitrogen, carbon monoxide or hydrogen.

If desired, the carbonylatable reactant may be contacted with a bed of alumina or corundum immediately before the bed of catalyst.

Preferably, the carbonylation process is carried out in the substantial absence of halides, such as iodide. By 'substantial absence' is meant that the combined halide content, such as the combined iodide content of any gaseous feeds and the catalyst are less than 500 ppm and preferably less than 100 ppm.

The carbonylation process may be carried out as a fixed bed, fluid bed or moving bed process.

The carbonylation process may be operated as a continuous or a batch process, preferably as a continuous process.

The product of the carbonylation process is acetic acid and/or methyl acetate. Where the carbonylatable reactant is methanol, the carbonylation product is acetic acid but methyl acetate may also be produced, depending on the extent of carbonylation.

Where the carbonylatable reactant is dimethyl ether the primary product of the process is methyl acetate but small amounts of acetic acid may also be produced.

The acetic acid produced by the process of the present invention can be removed in the form of a vapour and thereafter condensed to a liquid. The acetic acid can be subsequently purified using conventional techniques, such as distillation.

Where methyl acetate is a product of the process, at least some may be recovered from the carbonylation reaction products and sold as such. Alternatively some methyl acetate may be recycled to the carbonylation reactor and/or used, with or without further treatment, as a feedstock for other chemical processes. Suitably, at least a portion of the methyl acetate may be hydrolysed to acetic acid using known techniques such as reactive distillation in the presence of an acid catalyst.

During the course of carbonylation reactions which employ zeolite catalysts including mordenite catalysts, it is known that carbonaceous-type deposits tend to build-up on the catalyst and cause the catalyst to become at least partially deactivated. Typically, deactivated catalysts are subjected to a regeneration treatment to remove at least a portion of the carbonaceous deposits and restore at least some catalytic activity.

In accordance with the present invention, the copper and silver loaded mordenite catalyst is regenerated subsequent to its use in the carbonylation process.

It has now been found that mordenites loaded with a combination of copper and silver by ion-exchange, are more effectively regenerated than mordenites loaded with either silver or copper alone. This important property allows the copper and silver mordenite catalyst, after regeneration, to achieve a catalytic activity which is closer to its initial catalytic activity than a mordenite loaded with either copper or silver alone. More advantageously, the copper and silver loaded mordenite catalyst is more effectively regenerated than a mordenite loaded with either copper or silver alone even after multiple regenerations.

The regeneration of the catalyst may be carried out in-situ i.e. within the catalytic reactor. In this manner, it is not necessary to remove the catalyst from the reactor. Alternatively, the catalyst may be regenerated offsite.

Any suitable regeneration process may be used to regenerate the catalyst, such as the regeneration processes described, for example in WO2009/077745 and WO2009/077739.

The regenerated catalyst is preferably reused in the carbonylation process.

In one embodiment of the present invention, the catalyst may be regenerated in-situ using the following steps:
(i) ceasing contact of the catalyst with the carbonylatable reactant and the carbon monoxide-containing gas;
(ii) optionally purging the reactor with an inert gas;
(iii) regenerating the catalyst with a regenerating gas comprising a molecular oxygen-containing gas and an inert diluent;
(iv) terminating the regeneration;
(v) optionally purging the reactor with an inert gas; and
(vi) resuming contact of the catalyst with the carbonylatable reactant and a carbon monoxide-containing gas.

In step (iv) the regenerating gas comprises a molecular oxygen-containing gas and an inert diluent. The molecular oxygen-containing gas may be molecular oxygen, air or a gas richer or poorer in molecular oxygen than air. The inert diluent may be, for example, nitrogen, helium, argon, carbon dioxide or a mixture thereof.

Preferably, the regenerating gas comprises a mixture of oxygen or air and an inert diluent selected from at least one of nitrogen and carbon dioxide.

Suitably, the concentration of the molecular oxygen-containing gas in the regenerating gas may be in the range 0.1 mol % to 25 mol %, such as 0.5 to 20 mol % based on the total of the concentration of the molecular oxygen-containing gas and the concentration of the inert diluent.

Suitably, at a total pressure in the range 1 to 100 bar, the partial pressure of the molecular oxygen-containing gas may be, for example, less than 1.5 bar and preferably less than 1.0 bar.

The regeneration may be carried out at a temperature in the range 225 to 325° C., preferably in the range 250 to 300° C.

The regeneration may be carried out at a total pressure in the range 1 to 100 bar, such as 1 to 80 bar.

Suitably, the regeneration is carried out at a temperature in the range 250 to 300° C. and at a total pressure in the range 1 to 80 bar.

The gas hourly space velocity (GHSV) of the regeneration gas may suitably be in the range 500 to 10,000 $h^{-1}$.

Prior to starting the regeneration process and/or after terminating the regeneration process, the reactor may be purged with an inert gas, such as nitrogen and/or helium, to remove volatile components such as carbon monoxide, hydrogen, carbonylatable reactants carbonylation products and light hydrocarbons.

In a further embodiment, the regeneration may be carried out with a regenerating gas which comprises hydrogen or a mixture of hydrogen and carbon monoxide. Suitably, regeneration with hydrogen or a mixture of hydrogen and carbon monoxide may be carried as follows:
(a) ceasing contact of the catalyst with the carbonylatable reactant and optionally the carbon monoxide-containing gas;
(b) regenerating the catalyst with a regenerating gas selected from hydrogen and a mixture of hydrogen and carbon monoxide;
(c) terminating the regeneration; and
(d) resuming contact of the catalyst with the carbonylatable reactant and a carbon monoxide-containing gas.

Where a mixture of hydrogen and carbon monoxide is used as the regenerating gas, the gases may be fed into the reactor as individual feed streams, preferably, however, the two gases are employed as a single mixed feed stream.

Where the carbonylation process is carried out with synthesis gas it is advantageous to use this mixture as the regenerating gas. In such a case, it is not necessary to cease contact of catalyst with the carbon monoxide and hydrogen prior to regeneration. However, for use in the regeneration step, the partial pressure of the hydrogen may be adjusted.

Where hydrogen is used as the regenerating gas, contact of the catalyst with the carbon monoxide feed is ceased prior to regeneration.

Where hydrogen is used as the regenerating gas, the partial pressure of hydrogen may suitably be in the range 1 to 100 bar, such as 5 to 80 bar.

The gas hourly space velocity (GHSV) of hydrogen may suitably be in the range 500 to 10,000 $h^{-1}$, such as 2000 to 8000 $h^{-1}$.

Where the regenerating gas is a mixture of hydrogen and carbon monoxide, the molar ratio of hydrogen:carbon monoxide may be in the range 20:1 to 1:10, such as 5:1 to 1:5.

Where the regenerating gas is a mixture of hydrogen and carbon monoxide, the partial pressure of carbon monoxide may be in the range 0.1 to 80 bar, such as 5 to 65 bar, and the partial pressure of hydrogen may be in the range 0.1 to 99.9 bar, such as 5 to 80 bar.

The total gas hourly space velocity (GHSV) of hydrogen and carbon monoxide may be in the range 500 to 10,000 $h^{-1}$ such as 2000 to 8000 $h^{-1}$.

The regeneration may be carried out at a temperature in the range 250 to 600° C., suitably in the range 300 to 500° C.

The regeneration may be carried out at a total pressure in the range 1 to 100 bar, such as 1 to 80 bar.

Suitably, the regeneration is carried out at a temperature in the range 300 to 500° C. and at a total pressure in the range 1 to 80 bar.

After regeneration of the catalyst with hydrogen and optional carbon monoxide has been completed the carbonylation process is resumed by re-introducing the carbonylatable reactant feed, and a carbon monoxide-containing gas.

The period over which the catalyst is contacted with a regenerating gas (oxygen/diluent or hydrogen and optionally carbon monoxide) is chosen such that activity of the catalyst after regeneration is greater than the activity of the catalyst immediately prior to the start of the regeneration process. Typically, the contact period is in the order of hours, such as in the range 1 to 500 hours, for example 1 to 100 hours.

In the process of the present invention, the catalyst may be subjected to one or more regenerations, such as, 2 to 4 regenerations.

Each regeneration may be performed under the same or different regeneration conditions.

BRIEF DESCRIPTION OF THE DRAWINGS

FIG. 1 depicts the STY to methyl acetate product in g $l^{-1}$ $h^{-1}$ versus time on stream for Ag-mordenite, Cu-mordenite and Ag—Cu-mordenite catalysts prepared by ion-exchange.

The invention is now illustrated with reference to the following Example.

EXAMPLE 1

Catalyst Preparation

Catalyst A: Silver Mordenite

Silver mordenite was prepared by ion-exchange in accordance with the following procedure.

$NH_4$-mordenite (10 g) with a silica to alumina ratio of 20 (ex Zeolyst International) was added to a 100 ml autoclave bomb containing an aqueous solution of silver (I) nitrate (1.36 g) in deionised water (100 mL). The autoclave bomb was placed in an oven at 100° C. and stirred with rapid rotation for 3 hours. It was then removed from the oven and the mordenite/silver nitrate solution was filtered to recover solid silver mordenite. The silver mordenite was washed with excess deionised water before being dried at 90° C. for 2 hours and then calcined at 500° C. for 3 hours.

The silver mordenite was compacted at 10 tonnes in a 13 mm die set using a pneumatic press, and crushed and sieved to a particle size fraction of 125 to 160 microns. ICP spectroscopic analysis of the silver mordenite showed that it had a silver content of 5.2 wt % (equivalent to a silver loading of 39 mol % relative to aluminium) and an aluminium content of 3.3 wt %.

Catalyst B: Copper Mordenite

Copper mordenite was prepared by ion-exchange in accordance with the following procedure.

$NH_4$-mordenite (10 g) with a silica to alumina ratio of 20 (ex Zeolyst International) was treated with an aqueous solution of copper (II) nitrate hydrate (0.742 g) in deionised water (100 mL) and stirred at 80° C. for 2 hours to form a mordenite/copper nitrate solution which was then filtered to recover solid copper mordenite. The copper mordenite was washed with excess deionised water before being dried at 90° C. for 2 hours and then calcined at 500° C. for 3 hours.

The copper mordenite was compacted at 10 tonnes in a 13 mm die set using a pneumatic press, and crushed and sieved to a particle size fraction of 125 to 160 microns. ICP spectroscopic analysis of the copper mordenite showed that it had a copper content of 1.3 wt % (equivalent to a copper loading of 15 mol % relative to aluminium) and an aluminium content of 3.8 wt %.

Catalyst C: Copper/Silver Mordenite

Copper and silver mordenite was prepared by ion-exchange in accordance with the following procedure.

The preparation of Catalyst A (silver mordenite) was repeated to produce a dried (non-calcined) silver mordenite. The silver mordenite was added to a 100 ml autoclave bomb containing an aqueous solution of copper nitrate hydrate (0.742 g) in deionised water (100 mL). The autoclave bomb was placed in an oven at 100° C. and rotated rapidly for 2 hours to form a silver mordenite/copper nitrate solution which was then filtered to recover solid copper and silver mordenite. The copper and silver mordenite was washed with excess deionised water before being dried at 90° C. for 3 hours and calcined at 500° C. for 3 hours.

The copper and silver mordenite was compacted at 10 tonnes in a 13 mm die set using a pneumatic press, and crushed and sieved to a particle size fraction of 125 to 160 microns. ICP spectroscopic analysis of the copper and silver mordenite showed that it had a copper content of 1.2 wt %, (equivalent to a copper loading of 15 mol % relative to aluminum), a silver content of 4.3 wt % (equivalent to a silver loading of 31 mol % relative to aluminum) and an aluminium content of 3.5 wt %.

Carbonylation Using Catalysts A, B and C

The carbonylation of dimethyl ether, using each of Catalysts A, B and C, was carried out in a pressure flow reactor unit consisting of 16 identical reactors of the type described in WO 2005063372, and in accordance with the following procedure. Into a catalyst holder was placed a 5 cm bed of steatite of sieve fraction of 100-350 μm. A 5 cm corundum bed of sieve fraction of 125-160 μm was placed on top of the steatite bed. On a dry mass basis (determined by loss on ignition of the relevant sample measured by heating the sample from room temperature to 600° C. at a ramp rate of ca. 30° C. per minute), 0.625 g (1 ml) of a catalyst was placed on top of the corundum bed. The catalyst was covered by a 5 cm corundum bed of a particle size of 125-160 μm. A 5 cm steatite bed of sieve fraction of 100-350 μm was placed on top of the corundum bed. The catalyst was pressurised to a reaction pressure of 70 bar with carbon monoxide and hydrogen in a 4:1 molar ratio at a flow rate of 4 l/h. The catalyst was then heated at 0.5° C./min to 220° C. and held at this temperature for 3 hours. The temperature was then increased to 300° C. at 0.5° C./min and held at this temperature for 3 hours. A gaseous feed of carbon monoxide, hydrogen and dimethyl ether was then introduced into the reactor in a molar ratio of 72:18:10 and at a gas hourly space velocity (GHSV) of 4000 $h^{-1}$. The effluent stream from the reactor was continuously analysed by gas chromatography to determine the concentration of reactants and carbonylation products. The carbonylation process was conducted for a total of 335 hours. Four regenerations of each catalyst were carried out in-situ after 97, 147, 218 and 266 hours on stream in accordance with the Regeneration Procedure described below.

Regeneration Procedure

Contact of the catalyst with carbon monoxide, hydrogen and dimethyl ether was ceased and the reactor purged with nitrogen for 30 minutes. The reactor temperature was reduced to 250° C., after which, the catalyst was contacted with a gas comprising 1 vol % $O_2$ and 99 vol % $N_2$ at a GHSV of 4000 $h^{-1}$. After 13.5 hours, the oxygen content of the gas was increased to 2 vol %. The catalyst was contacted with this gas for 4 hours, after which time, the contact of the catalyst with the gas was ceased and the reactor purged with nitrogen for 30 minutes. Prior to resuming contact of the catalyst with carbon monoxide, hydrogen and dimethyl ether (at a molar ratio of 72:18:10 and a GHSV of 4000 $h^{-1}$), the temperature of the reactor was raised to 300° C.

The results of Example 1 are shown in FIG. 1 which shows the space time yield (STY) to methyl acetate (g $l^{-1}$ $h^{-1}$) achieved by Catalysts A, B and C, before regeneration, and also subsequent to each of four regenerations. Prior to regeneration, Catalyst C (copper and silver mordenite) exhibits a higher STY than either Catalyst A (silver mordenite) or Catalyst B (copper mordenite). After each regeneration, Catalyst C is returned to a significantly higher STY than either Catalyst A or Catalyst B.

The invention claimed is:

1. A process for the production of at least one of methyl acetate and acetic acid which process comprises contacting in a reactor a carbon monoxide-containing gas and a carbonylatable reactant selected from at least one of methanol and reactive derivatives thereof with a catalyst which comprises a mordenite loaded with copper and silver, the loading of the copper and silver being carried out by ion-exchange of part or all of the cation-exchangeable sites of the mordenite with copper and silver ions, to produce at least one of methyl acetate and acetic acid and subsequently regenerating the catalyst;
   wherein the loading of copper and silver is carried out onto a mordenite which is in the ammonium form or in the proton form: and further
   wherein the catalyst is regenerated by
   (i) ceasing contact of the catalyst with the carbonylatable reactant and the carbon monoxide-containing gas;
   (ii) optionally purging the reactor with an insert gas;
   (iii) regenerating the catalyst with a regenerating gas comprising a molecular oxygen-containing gas and an inert diluent;
   (iv) terminating the regeneration;
   (v) optionally purging the reactor with an inert gas; and
   (vi) resuming contact of the catalyst with the carbonylatable reactant, and a carbon monoxide-containing gas.

2. A process according to claim 1 wherein the loading of copper and silver onto mordenite is carried out by sequential ion-exchange.

3. A process according to claim 1 wherein the mordenite is loaded with copper in an amount in the range 5 to 30 mol % relative to aluminium and silver in an amount in the range 5 to 50 mol % relative to aluminium.

4. A process according to claim 1 wherein the loading of copper and silver onto mordenite is carried out in accordance with the steps:
   (1) contacting the mordenite with at least one aqueous solution of a metal salt selected from copper and/or silver salts until the mordenite is at or above its level of incipient wetness
   (2) filtering the contacted mordenite to obtain a solid copper and/or silver loaded mordenite
   (3) washing the copper and/or silver loaded mordenite with a solvent
   (4) drying the washed copper and/or silver loaded mordenite
   (5) where necessary, steps (1) to (5) are repeated so as to obtain a mordenite loaded with both copper and silver.

5. A process according to claim 4 wherein prior to filtering the contacted mordenite of step 2, the contacted mordenite is heated and wherein the dried catalyst of step 4 or step 5 is calcined.

6. A process according to claim 1 wherein the regeneration is carried out at 225 to 325° C.

7. A process according to claim 1 wherein the regenerating gas has a concentration of molecular oxygen-containing gas in the range 0.1 mol % to 25 mol % based on the total concentrations of the molecular oxygen-containing gas and the inert diluent.

8. A process for the production of at least one of methyl acetate and acetic acid which process comprises contacting in a reactor a carbon monoxide-containing gas and a carbonylatable reactant selected from at least one of methanol and reactive derivatives thereof with a catalyst which comprises a mordenite loaded with copper and silver, the loading of the cooper and silver being carried out by ion-exchange of part or all of the cation-exchangeable sites of the mordenite with copper and silver ions, to produce at least one of methyl acetate and acetic acid and subsequently regenerating the catalyst;
   wherein the regeneration is carried out by:
   (a) ceasing contact of the catalyst with the carbonylatable reactant and optionally the carbon monoxide-containing gas;

(b) regenerating the catalyst with a regenerating gas selected from hydrogen or a mixture of hydrogen and carbon monoxide;
(c) terminating the regeneration; and
(d) resuming contact of the catalyst with the carbonylatable reactant and a carbon monoxide-containing gas.

9. A process according to claim 1 wherein the regeneration is carried out in-situ.

10. A process according to claim 1 wherein the catalyst is subjected to one or more regenerations.

11. A process according to claim 1 wherein the carbonylatable reactant is dimethyl ether and water is present in gaseous carbonylatable reactant(s) in an amount of less than 2.5 wt %, relative to the amount of dimethyl ether.

12. A process according to claim 1 wherein the carbon monoxide-containing gas comprises carbon monoxide and hydrogen.

13. A process according to claim 1 wherein methyl acetate is a product and at least a portion of it is hydrolysed to acetic acid.

14. A process according to claim 8 wherein the loading of copper and silver is carried out onto a mordenite which is in the ammonium form or in the proton form.

15. A process according to claim 8 wherein the loading of copper and silver onto mordenite is carried out by sequential ion-exchange.

16. A process according to claim 8 wherein the mordenite is loaded with copper in an amount in the range 5 to 30 mol % relative to aluminium and silver in an amount in the range 5 to 50 mol % relative to aluminium.

17. A process according to claim 8 wherein the loading of copper and silver onto mordenite is carried out in accordance with the steps:

(1) contacting the mordenite with at least one aqueous solution of a metal salt selected from copper and/or silver salts until the mordenite is at or above its level of incipient wetness
(2) filtering the contacted mordenite to obtain a solid copper and/or silver loaded mordenite
(3) washing the copper and/or silver loaded mordenite with a solvent
(4) drying the washed copper and/or silver loaded mordenite
(5) where necessary, steps (1) to (5) are repeated so as to obtain a mordenite loaded with both copper and silver.

18. A process according to claim 17 wherein prior to filtering the contacted mordenite of step 2, the contacted mordenite is heated and wherein the dried catalyst of step 4 or step 5 is calcined.

19. A process according to claim 8 wherein the regeneration is carried out in-situ.

20. A process according to claim 8 wherein the catalyst is subjected to one or more regenerations.

21. A process according to claim 8 wherein the carbonylatable reactant is dimethyl ether and water is present in gaseous carbonylatable reactant(s) in an amount of less than 2.5 wt %, relative to the amount of dimethyl ether.

22. A process according to claim 8 wherein the carbon monoxide-containing gas comprises carbon monoxide and hydrogen.

23. A process according to claim 8 wherein methyl acetate is a product and at least a portion of it is hydrolysed to acetic acid.

* * * * *